(12) United States Patent
Poore

(10) Patent No.: US 7,660,616 B1
(45) Date of Patent: Feb. 9, 2010

(54) IMPLANTABLE MULTI-WAVELENGTH OXIMETER SENSOR

(75) Inventor: John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 808 days.

(21) Appl. No.: 11/231,555

(22) Filed: Sep. 20, 2005

(51) Int. Cl.
*A61B 5/1455* (2006.01)

(52) U.S. Cl. ....................................... 600/341

(58) Field of Classification Search ................. 600/310, 600/322, 323, 324, 325, 327, 332, 339, 341
See application file for complete search history.

(56) References Cited

U.S. PATENT DOCUMENTS

| | | | |
|---|---|---|---|
| 3,847,483 A | 11/1974 | Shaw et al. | 356/41 |
| 4,114,604 A | 9/1978 | Shaw et al. | 128/2 L |
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PT |
| 4,788,980 A | 12/1988 | Mann et al. | 128/419 PG |
| 4,809,697 A | 3/1989 | Causey, III et al. | 128/419 PT |
| 4,815,469 A | 3/1989 | Cohen et al. | |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 4,969,467 A | 11/1990 | Callaghan et al. | 128/419 PG |
| 5,350,410 A | 9/1994 | Kleks et al. | 607/28 |
| 5,553,615 A | 9/1996 | Carim et al. | 128/633 |
| 5,608,207 A | 3/1997 | Allen et al. | |
| 6,275,734 B1 | 8/2001 | McClure et al. | 607/27 |
| 6,289,229 B1 * | 9/2001 | Crowley | 600/310 |
| 6,491,639 B1 | 12/2002 | Turcott | |
| 6,526,298 B1 | 2/2003 | Khalil et al. | |
| 6,561,984 B1 | 5/2003 | Turcott | |
| 6,567,678 B1 * | 5/2003 | Oosta et al. | 600/316 |
| 6,662,031 B1 | 12/2003 | Khalil et al. | |
| 6,731,967 B1 | 5/2004 | Turcott | 600/407 |
| 7,146,203 B2 | 12/2006 | Botvinick et al. | |
| 7,230,222 B2 | 6/2007 | Cheng et al. | |
| 2002/0026106 A1 * | 2/2002 | Khalil et al. | 600/310 |
| 2005/0027178 A1 * | 2/2005 | Iddan | 600/339 |
| 2007/0060811 A1 | 3/2007 | Roberts | |

OTHER PUBLICATIONS

Bornzin, Gene A. et al., "Measuring Oxygen Saturation and Hematocrit Using a Fiberoptic Catheter," IEEE Ninth Annual Conf of Eng & Biol Soc. 1987:0807-0809.

* cited by examiner

*Primary Examiner*—Eric F Winakur
*Assistant Examiner*—Etsub D Berhanu

(57) ABSTRACT

Implantable multi-wavelength oximetry sensors, which can be used to monitor a patient's blood oxygen saturation level, are described. The sensor includes an implantable sensor housing within which are located a plurality of light sources that each transmits light of a different wavelength. Also within the sensor housing are one or more surfaces that are configured to combine the light from the plurality of light sources into a beam of light for transmission through a portion of the housing (e.g., a window) through which light can exit and enter the housing. Additionally, a light detector is located within the sensor housing, to detect light scattered by blood back into the housing. This description is not intended to be a complete description of, or limit the scope of, the invention. Other features, aspects, and objects of the invention can be obtained from a review of the specification, the figures, and the claims.

27 Claims, 12 Drawing Sheets

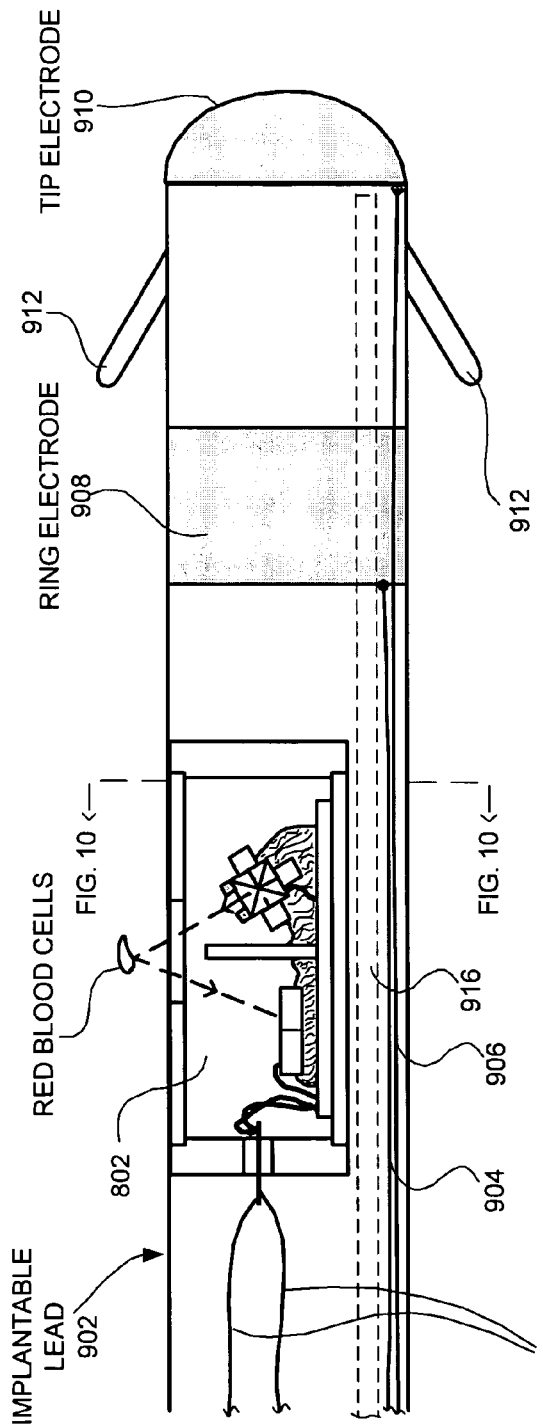
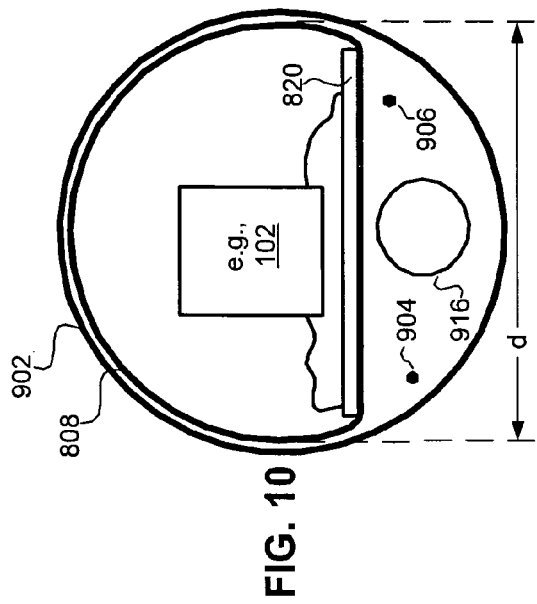
FIG. 9
FIG. 10

IMPLANTABLE MULTI-WAVELENGTH OXIMETER SENSOR

FIELD OF THE INVENTION

Embodiments of the present invention relate to implantable apparatuses that are useful for obtaining measures of blood oxygen saturation.

BACKGROUND

Blood oxygen saturation is the relative amount of oxygenated hemoglobin in all of the hemoglobin present in the blood stream. This hemoglobin is packaged in biconcave discs of approximately 10 micrometers diameter which commonly occur with a density of approximately five million red blood cells per cubic millimeter. When radiant energy (e.g., light) is incident upon red blood cells, the red blood cells both scatter and transmit the incident radiant energy. The differential absorption by oxygenated and non-oxygenated hemoglobin of the radiant energy reflected by and transmitted through the red blood cells furnishes the basis for the oxygen saturation measurements.

More specifically, pulse oximeters use light of two or more different centered wavelengths to obtain measures of blood oxygen saturation by measuring the absorption and/or scattering of oxyhemoglobin and reduced hemoglobin. The measured scattering data allows for the calculation of the relative concentrations of reduced hemoglobin and oxyhemoglobin, and therefore blood oxygen saturation levels, since the scattering relationships are known.

Most multi-wavelength pulse oximeters are non-implantable devices that are clipped onto a patient's finger or ear lobe. However, it is believed that it would be beneficial to chronically implant pulse oximeters so that measures of oxygen saturation and hematocrit (the density of red blood cells) can be used as feedback for pacing optimization, disease monitoring, and the like.

Some multi-wavelength implantable oximeter catheters are known, as can be appreciated from U.S. Pat. Nos. 3,847,483 and 4,114,604, each of which are incorporated herein by reference. For multi-wavelength oximeters to work properly, light from two or more light sources (e.g., from 670, 700 and 805 nm wavelength LEDs) should be combined into a single beam, to assure that the computed oxygen saturation is accurate with varying blood flow rate, pH, hematocrit and hemoglobin. In the devices of the '483 and '604 patents, fiber optic guides are used to combine the light of multiple wavelengths into the single beam. This, however, requires significant physical space. Thus, in the devices of the '482 and '604 patents, the light sources and fiber optic guides are located in a housing that is a distance from the measurement site, and optical fibers that are within a catheter are used to deliver the combined light beam to the measurement site at the distal end of the catheter.

It would be beneficial if an implantable optical combiner requiring less physical space can be provided, thereby enabling the optical combiner to be located at the measurement site.

SUMMARY

Certain embodiments described herein are directed to implantable multi-wavelength oximetry sensors, which can be used to monitor a patient's blood oxygen saturation level. In accordance with an embodiment, the sensor includes an implantable sensor housing within which are located a plurality of light sources that each transmits light of a different wavelength. Also within the sensor housing are one or more surfaces that are configured to combine the light from the plurality of light sources into a single beam of light for transmission through a portion of the housing (e.g., a window) through which light can exit and enter the housing. Additionally, a light detector is located within the sensor housing, to detect light scattered by blood back into the housing.

In accordance with another embodiment, the surface(s), which combine the light from the plurality of light sources into a single beam, are dichroic surface(s) that reflect light of certain wavelengths and pass light of other wavelengths. It is also possible that a surface rely on critical angle reflection to selectively reflect and pass light. Such surfaces can be formed on one more prism, or on one or more panel.

In accordance with another embodiment, the plurality of light sources include a first light source to transmit light having a first wavelength (e.g., 670 nm), a second light source to transmit light having a second wavelength (e.g., 700 nm) and a third light source to transmit light having a third wavelength (e.g., 805 nm). One dichoric surface reflects light of one of the three wavelengths and passes light of the other two wavelengths, while another dichroic surface reflects light of a different one of the three wavelengths and passes light of the other two wavelengths. Additionally, the dichroic surfaces and the light sources are positioned relative to one another such that light of the first wavelength, light of the second wavelength and light of the third wavelength are reflected by and/or pass through the dichroic surfaces to all travel in a same direction (for transmission through the window of the sensor housing). Embodiments of the present invention are also directed to sensors with only two light sources, as well as to sensors with more than three light sources, as will be appreciated from the detailed description.

In accordance with another embodiment, the implantable sensor housing is sized to fit within an implantable catheter or cardiac lead. Embodiments of the present invention are also directed to implantable catheters and leads that include the multi-wavelength oximetry sensors described above. In such embodiments, electrical wires run through the catheter or lead to an implantable cardiac device (e.g., monitor, pacemaker and/or defibrillator) to which one end of the catheter or lead is attached, to thereby connect the light sources and light detector to the implantable cardiac device. A benefit of embodiments of the present invention is that there is no need for optical fibers to run through the lead or catheter. Another benefit of embodiments of the present invention is that an optical combiner can be located at the measurement site.

This summary is not intended to be a complete description of the invention. Other features, aspects, objects and advantages of the invention can be obtained from a review of the specification, the figures, and the claims.

BRIEF DESCRIPTION OF THE DRAWINGS

FIG. 9 illustrates an implantable lead that includes the sensor of FIG. 8A, in accordance with an embodiment of the present invention.

FIG. 10 illustrates a rough cross-section of the lead shown in FIG. 9.

DETAILED DESCRIPTION

Figure 1:
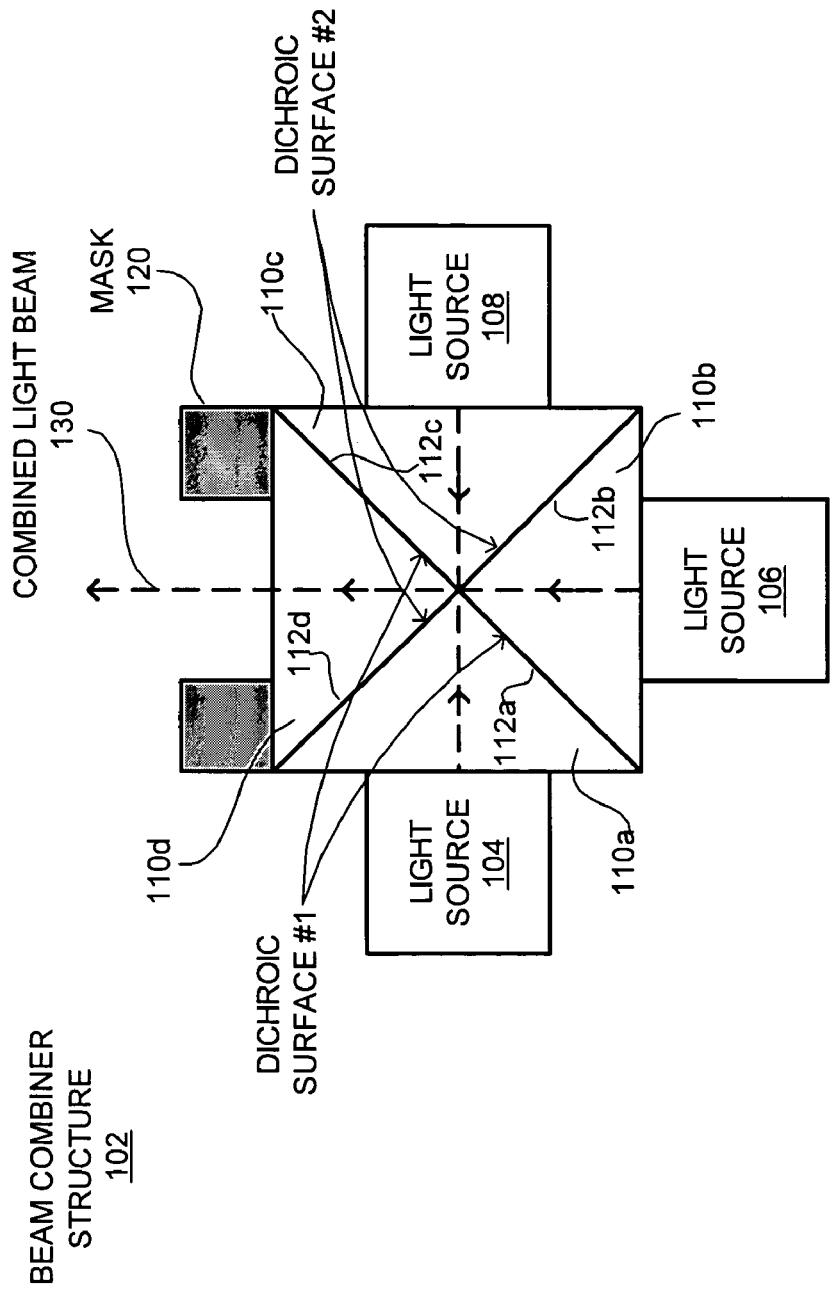
FIG. 1 illustrates an apparatus for combining light of three different wavelengths from three physically separate light sources, according to an embodiment of the present invention.

The following description includes the best modes presently contemplated for practicing the various embodiments. This description is not to be taken in a limiting sense but is made merely for the purpose of describing the general principles of the illustrative embodiments. The scope of the invention should be ascertained with reference to the claims. In the description that follows, like numerals or reference designators will be used to refer to like parts or elements throughout. Also, the left-most digit(s) of a reference number identifies the drawing in which the reference number first appears.

FIG. 1 shows a first embodiment of the present invention that combines light of three different wavelengths from three physically separate miniature light sources using dichroic surfaces. Such dichroic surfaces are likely dichroic mirrors, but can be dichroic filters, or combinations thereof. Dichroic surfaces have the property of reflecting light of specific wavelengths and passing light of other wavelengths.

Referring to FIG. 1, a beam combiner structure 102, in accordance with an embodiment of the present invention, includes three physically separate light sources 104, 106 and 108, each of which produces radiation of a different wavelength (e.g., 670, 700 and 805 nm). The light sources are preferably light emitting diodes (LEDs), but can be other less preferable sources such as, but not limited to, laser diodes and incandescent lamps. The light sources are shown as being mounted to a structure (a cube in this example) which is made up of four triangular prisms 110a, 110b, 110c and 110d that are bonded together, e.g., using an optical cement or some other clear epoxy resin. Appropriate sides of the prisms are coated to thereby form a pair of dichroic surfaces, labeled dichroic surface #1 and dichroic surface #2. There are multiple ways this can be accomplished. However, it is believed that the most cost effective way is to have only one side of each prism 110a, 110b, 110c and 110d have a dichroic coating. For example, side 112a of prism 110a and side 112c of prism 110c can be coated to form dichroic surface #1, and side 112b of prism 110b and side 112d of prism 110d can be coated to form dichroic surface #2. While the prisms are likely made of glass, other suitable materials may be used, such as, but not limited to, plastics.

In accordance with an embodiment of the present invention, the dichroic surface #1 will reflect the wavelength ($\lambda_1$) generated by the light source 104, and pass the wavelengths ($\lambda_2$ and $\lambda_3$) generated by light sources 106 and 108. Similarly, the dichroic surface #2 will reflect the wavelength ($\lambda_3$) generated by the light source 108, and pass the wavelengths ($\lambda_1$ and $\lambda_2$) generated by light sources 104 and 106. This can be explained in more detail using an example where the wavelength generated by light source 104 is 670 nm, the wavelength generated by light source 106 is 700 nm, and the wavelength generated by light source 108 is 805 nm (e.g., $\lambda_1$, $\lambda_2$ and $\lambda_3$ are, respectively, 670 nm, 700 nm and 805 nm). Continuing with this example, the present invention can be implemented if dichroic surface #1 reflects light below 685 nm and passes light above 685 nm, and dichroic surface #2 reflects light above 750 nm and passes light below 750 nm.

Still referring to FIG. 1, the dichroic surface #1 and the dichroic surface #2 and the light sources 104 and 108 are positioned (including angled) relative to on another such that light transmitted by the light source 104 is reflected by the dichroic surface #1 to travel in generally a same direction as light transmitted by the light source 108 that is reflected by the dichroic surface #2, as can be appreciated from the dashed lines shown. Additionally, the light source 106 is positioned such that its light, which passes through the dichroic surfaces #1 and #2, travels in generally the same direction as the just mentioned reflected light, as can also be appreciated from the dashed lines shown.

In practice, the light sources 104, 106 and 108 are serially energized, in a non-overlapping temporal relationship. In the manner just described, the light of wavelengths $\lambda_1$, $\lambda_2$ and $\lambda_3$ are combined into a single combined beam 130 that is transmitted toward patient tissue that includes red blood cells. The light of different wavelengths ($\lambda_1$, $\lambda_2$, and $\lambda_3$) are combined into the single beam so that the light of each wavelength shines equally on nearby red blood cells, to thereby increase the likelihood that the computed oxygen saturation is accurate with varying blood flow rate, pH, hematocrit and hemoglobin. A mask 120 may be used to reduce internal reflections.

When transmitted toward patient tissue, some of the light energy is scattered by blood. The different wavelengths are differently scattered, depending on the oxygen saturation level of the blood. After being scattered by blood, the interleaved light stream is received by a light detector (discussed below in more detail with reference to FIG. 8), which preferably produces a separate signal for each of the wavelengths. At a high level, time multiplexing is used to produce a signal path for each of the different wavelengths ($\lambda_1$, $\lambda_2$ and $\lambda_3$) of received light. Each signal path will typically include one or more filters and an A/D converter to sample the received light signals. Using electronic circuitry, firmware and/or software, the received light signals can be analyzed so that oxygen saturation levels can be determined in any well known manner, or in any manner devised in the future.

While three-wavelength pulse oximetry provides more accuracy than two-wavelength pulse oximetry, the accuracy obtained using two-wavelength pulse oximetry is satisfactory for many applications. Accordingly, in accordance with embodiments of the present invention, one of the light sources 104, 106 and 108 can be eliminated. If light source 106 is eliminated, then two dichroic surfaces are still needed, as can be appreciated from FIG. 3. However, if light source 104 (or light source 108) is eliminated, then only a single dichroic surface is necessary, as shown in FIG. 2.

Figure 2:
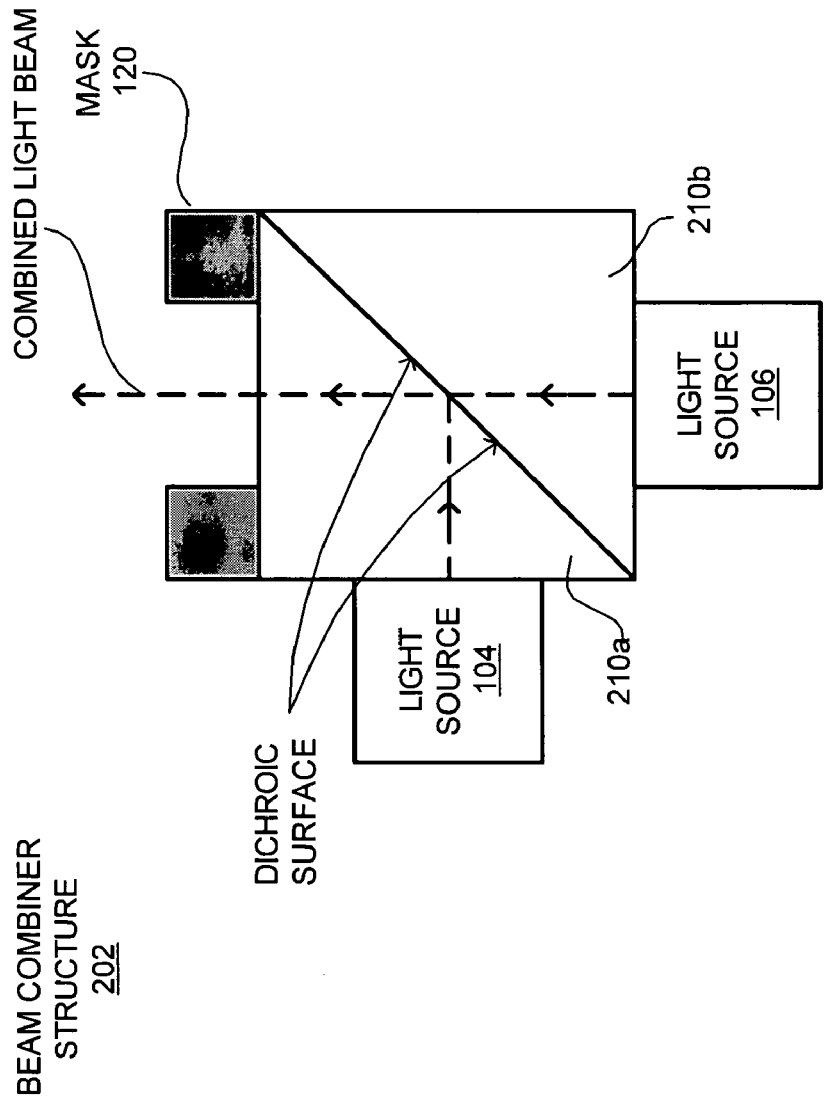
FIG. 2 illustrates an apparatus for combining light of two different wavelengths from two physically separate light sources, according to an embodiment of the present invention.

Referring to FIG. 2, the single dichroic surface reflects the wavelength generated by the light source 104 and passes the wavelength generated by the light source 106. Since only one dichroic surface is used, the assembly of prisms can be simplified. More specifically, the structure (also a cube in this example) can be made up of only two triangular prisms 210a and 210b.

Figure 3:
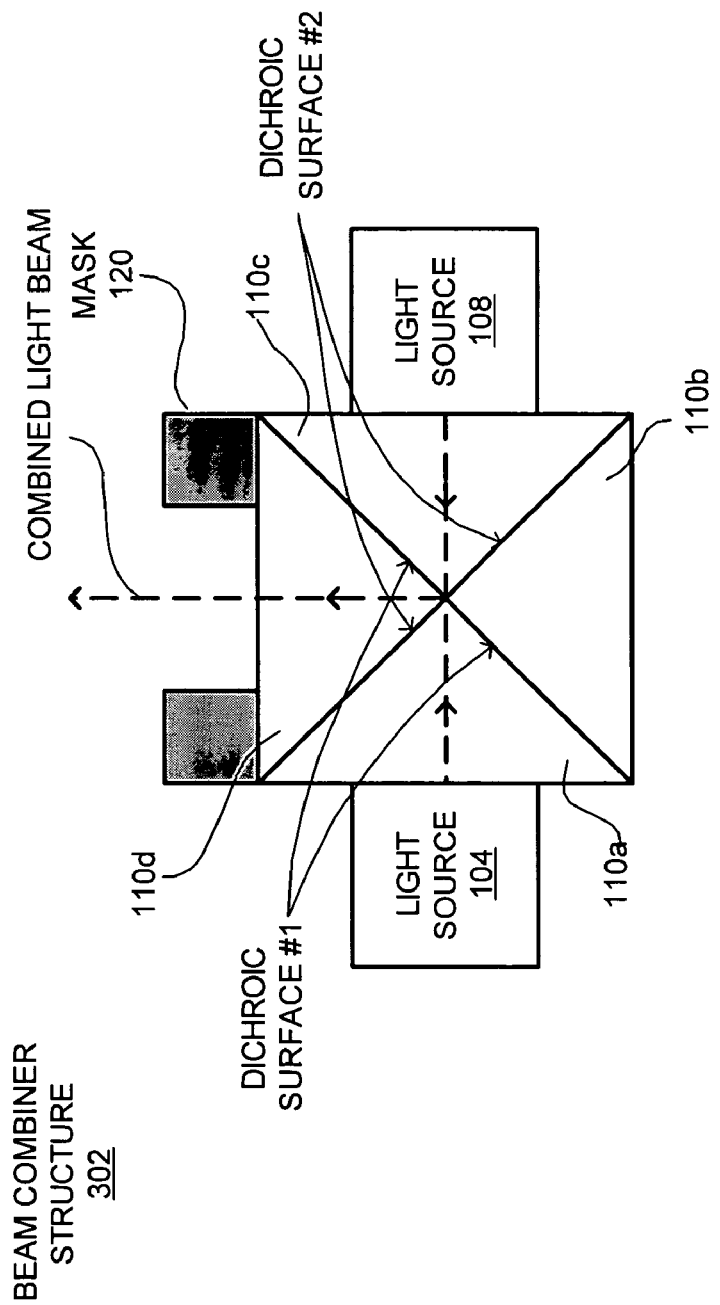
FIG. 3 illustrates an apparatus for combining light of two different wavelengths from two physically separate light sources, according to another embodiment of the present invention.
Figure 4:
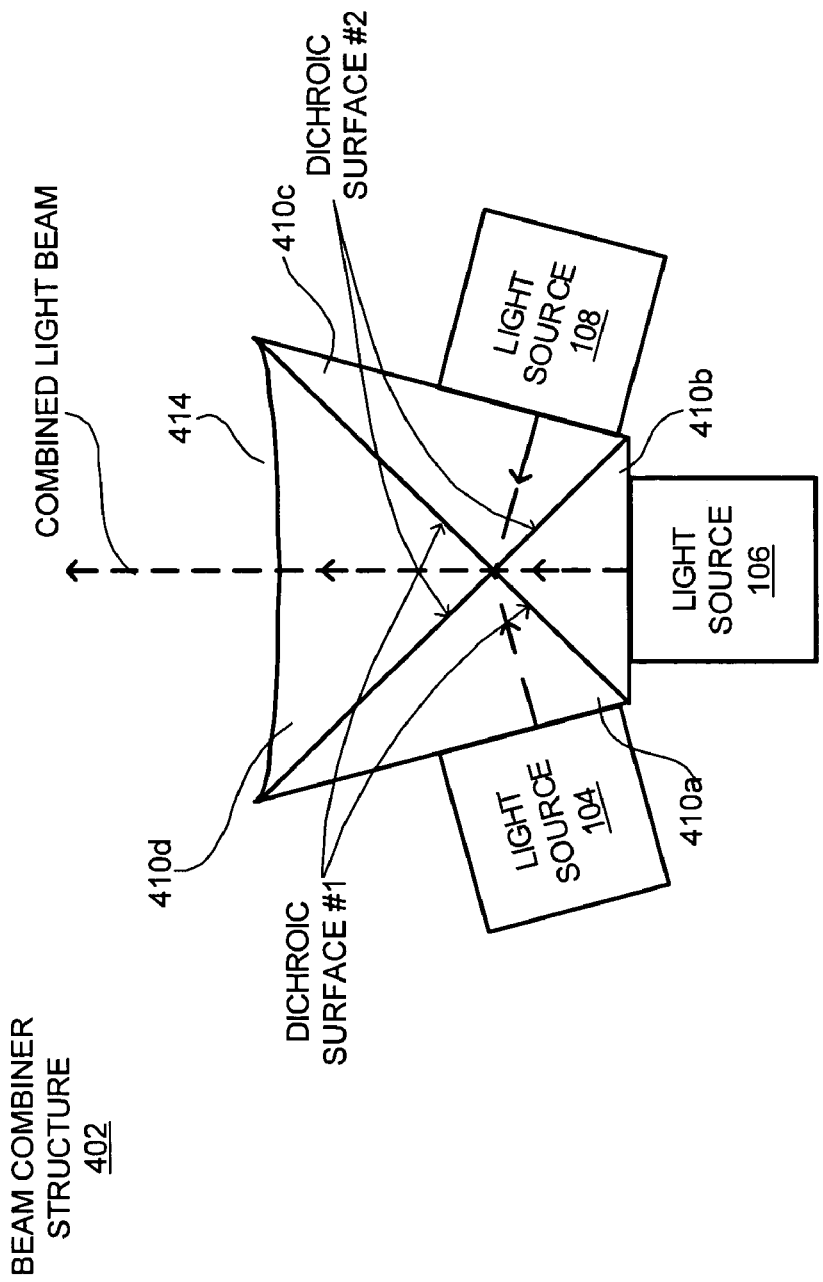
FIG. 4 illustrates an apparatus for combining light of three different wavelengths from three physically separate light sources, according to still another embodiment of the present invention.

In FIGS. 1, 2 and 3, the overall structures, formed from multiple prisms, were shown as being cubic. While embodiments of the present invention encompass such cubic structures, they should not be limited thereto. For example, other shapes, such as the ones shown in FIGS. 4 and 6, can be used. As can be seen from FIG. 4, the prisms 410a, 410b, 410c and 410d that make up the structure form a shape that resembles a trapezoid. Also shown in FIG. 4 is that not all outer sides of the structure need be flat. More specifically, in this example, the outer side 414 of prism 410d, through which the combined light beam travels, is shown as being concave, to increase the exit angle. Also shown in FIG. 4 is that not all of the prisms need be of the same size and shape.

Figure 5:
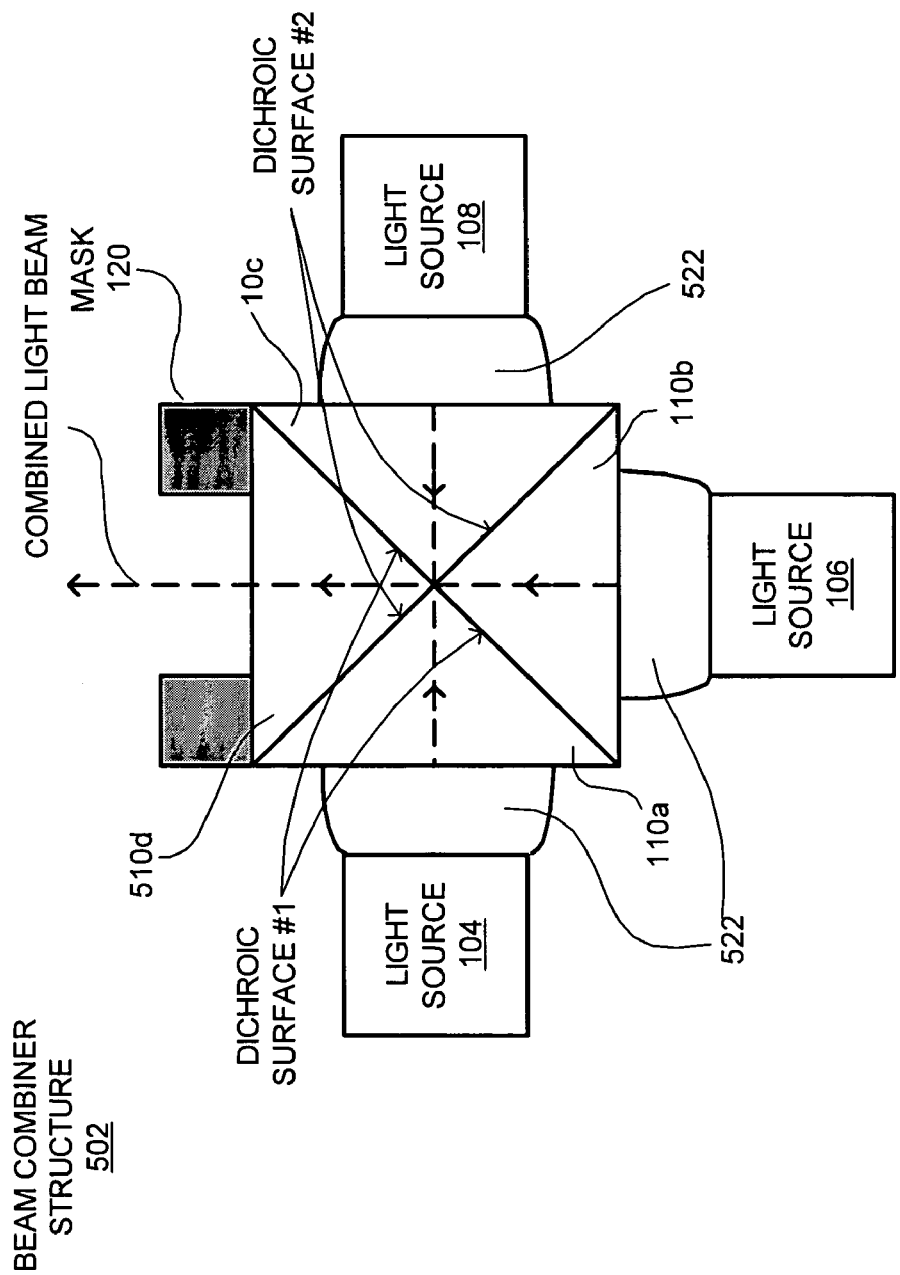
FIG. 5 illustrates an apparatus similar to the one shown in FIG. 1, but with the addition of combiner lenses between the light sources and prisms.

Referring now to FIG. 5, in accordance with an embodiment of the present invention, combiner lenses 522 can added for reducing the emitted light angle before the light is combined by the dichroic surfaces. Such lenses 522 can be added in any of the embodiments described herein.

Figure 6:
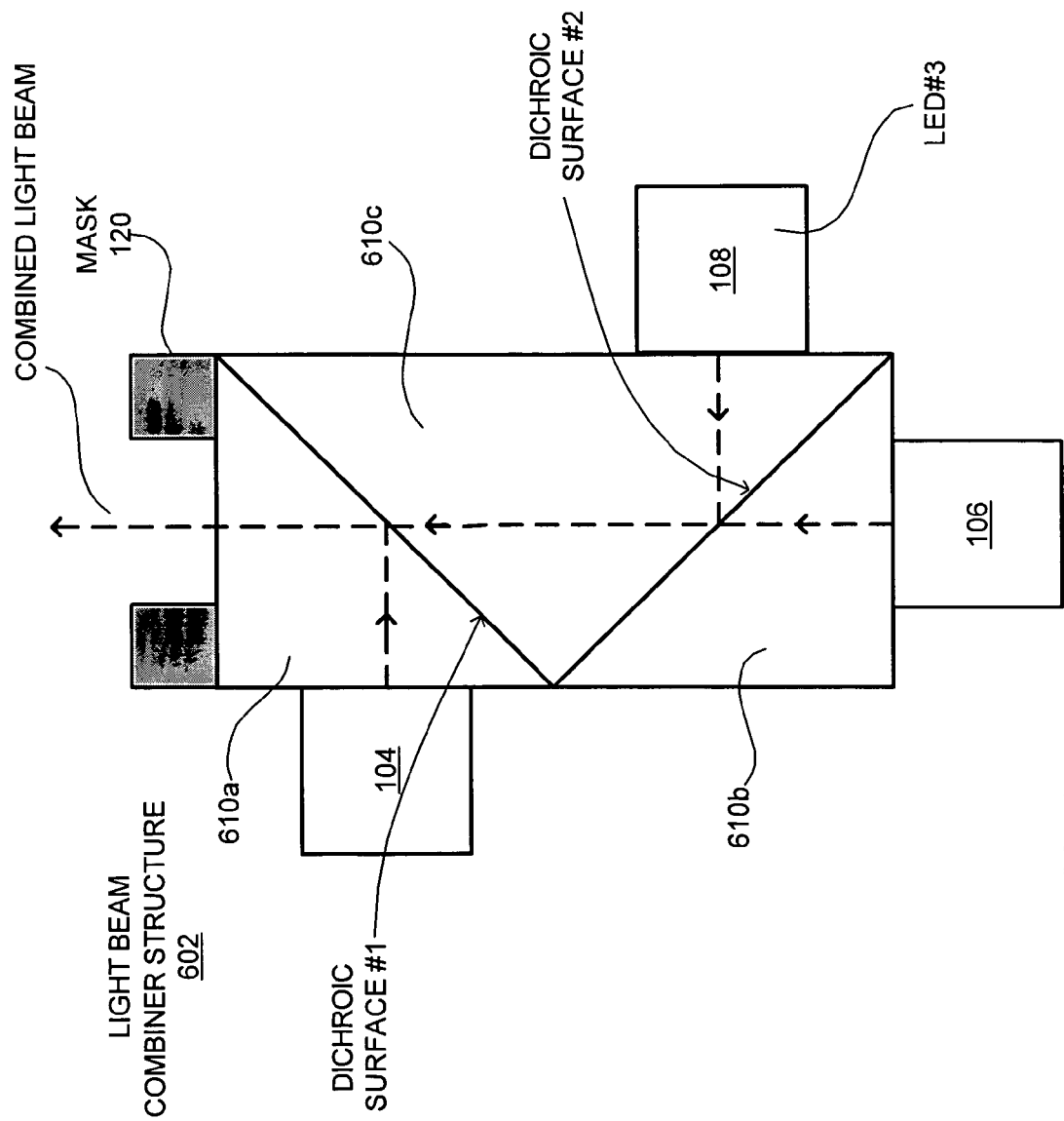
FIG. 6 illustrates an apparatus for combining light of three different wavelengths from three physically separate light sources, according to a further embodiment of the present invention.

FIG. 6 illustrates a variant of the present invention that has a simpler but likely somewhat larger overall size than the structure shown in FIG. 1. In this embodiment, only three prisms 610a, 610b and 610c are used to form a three-dimensional rectangular structure. Another difference is that the pair of dichroic surfaces does not intersect each other, as was the case in the previously discussed embodiments where there were three light sources. The beam combining structure 602 functions in a similar manner as the other structures discussed above. That is, dichroic surface #1 reflects the wavelength of light generated by the light source 104, and passes the wavelengths of light generated by the light sources 106 and 108. The dichroic surface #2 reflects the wavelength of light generated by the light source 108 and passes the wavelength of light generated by the light source 106. Because the light generated by the light source 104 is not incident upon the dichroic surface #2, it is not required that the dichroic surface #2 pass the wavelength generated by the light source 104, but it is allowed.

In the above discussed FIGS. 1 through 6, the dichroic surfaces were described as being formed on sides of prisms. The use of such structures is beneficial because the prisms can be bonded together to form a sturdy structure to which the light sources can be securely attached, as shown in the FIGS. However, in alternative embodiments, explained below with reference 7, this need not be the case.

Figure 7:
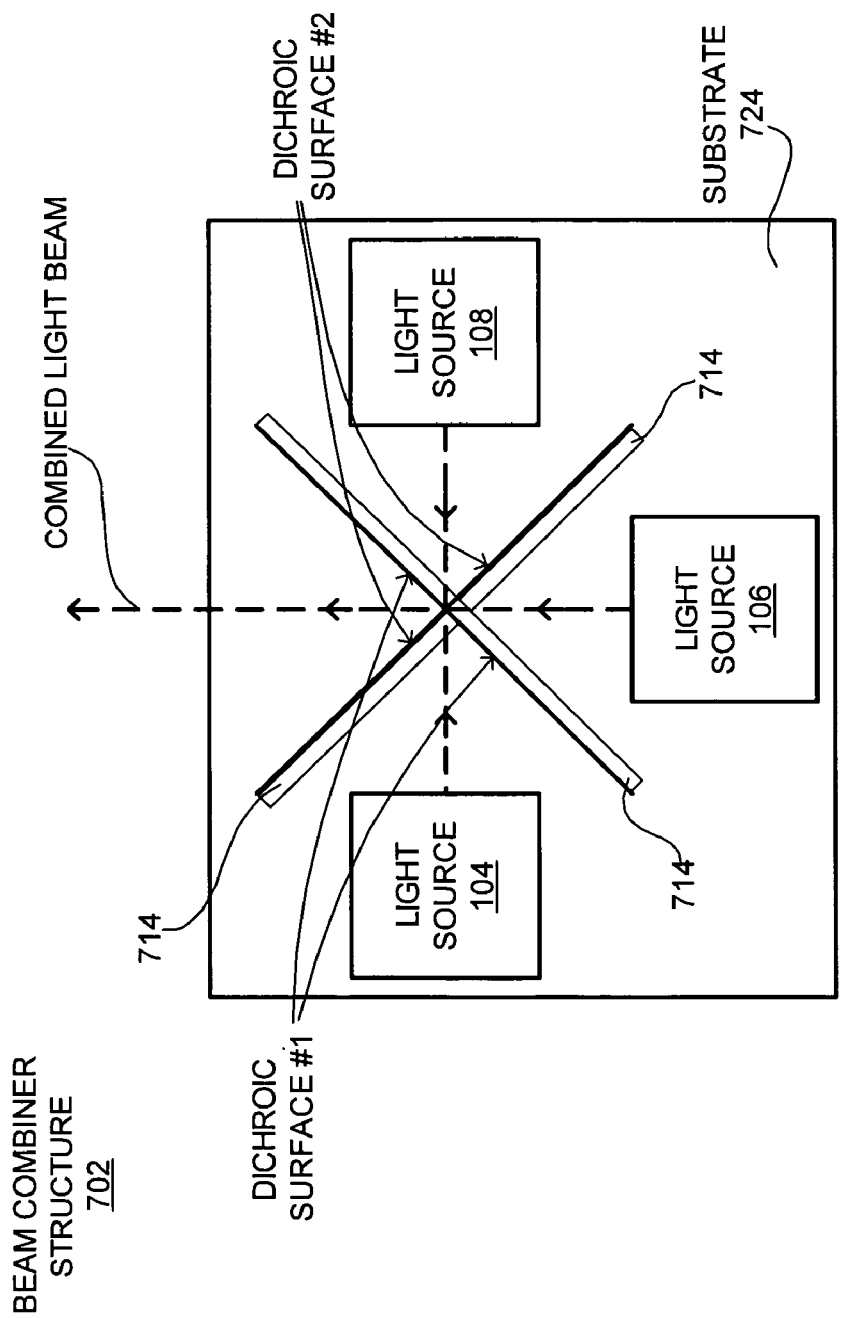
FIG. 7 illustrates how panels can be used in place of prisms.

Referring to FIG. 7, rather than using prisms, panels 714 are attached on at least one edge to a substrate 724, and dichroic surface(s) are formed on sides of the panels 714. While the panels 714 are likely made of glass, other suitable materials such as plastics may be used. (For FIG. 7, picture the substrate 724 being in the same plane as the page, and panels 714 extending perpendicularly out of the page.) In this embodiment, rather than securing the light sources 104, 106 and 108 to prisms, as could be done in the previously discussed embodiments, the light sources 104, 106 and 108 are secured to the same substrate 724 to which the panels 714 are secured. As was discussed above with reference to FIGS. 2 and 3, one of the light sources can be eliminated if two-wavelength pulse oximetry is to be used. Further, as was explained with reference to FIG. 2, if the light source to be eliminated is light source 104 or 108, then only one dichroic surface is required, which can be implemented using a single panel 714. In a similar manner as was described above with reference to FIGS. 4 and 6, the light sources and dichroic surfaces can be repositioned, so long as the arrangement results in the light of various wavelengths generally being combined into a single beam. Further, as was described with reference to FIG. 5, combiner lenses 522 can be added to the configuration shown in FIG. 7.

While the above described embodiments included either two or three separate light sources, one of ordinary skill in the art would understand, based on the above description, that light from more than three light sources can be combined in a similar manner. Accordingly, it is within the spirit and scope of the present invention that more than three light sources and more than two dichroic surfaces can be used. Such embodiments can be used for multi-wavelength oximetry that uses more than three wavelengths.

In accordance with other embodiments of the present invention, critical angle reflectors could be used instead of dichroic surfaces to accomplish combining of light from the two or more separate light sources. The critical angle is the largest angle off a surface at which light will be totally reflected from the surface. Sides of prisms or panels can positioned relative to light sources such that light of two or more wavelengths, from two or more separate light sources, can be combined into a single beam in much that same way as was described above with the use of dichroic surfaces.

Figure 8A:
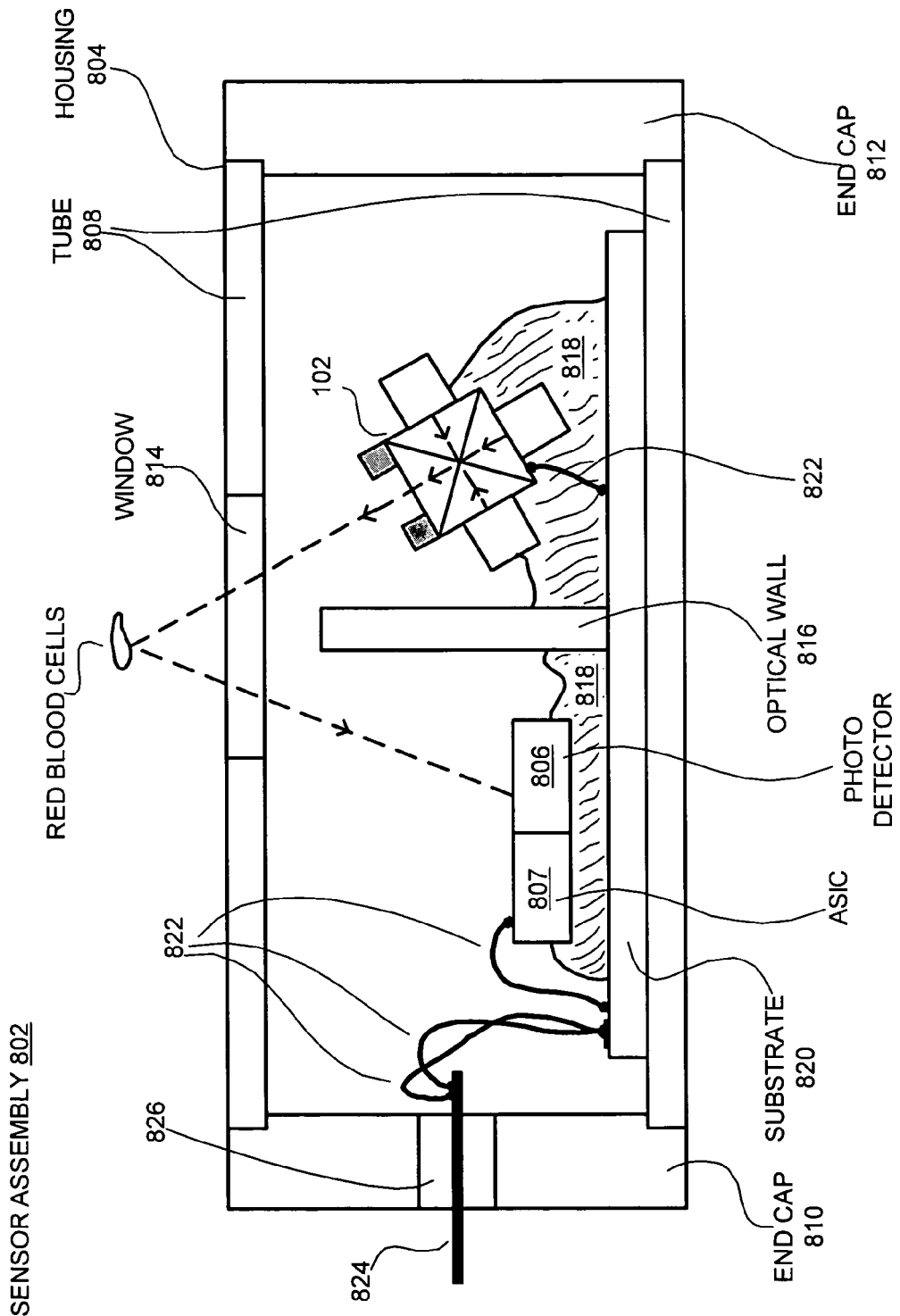
FIG. 8A illustrates an implantable oximetry sensor, according to an embodiment of the present invention.
Figure 8B:
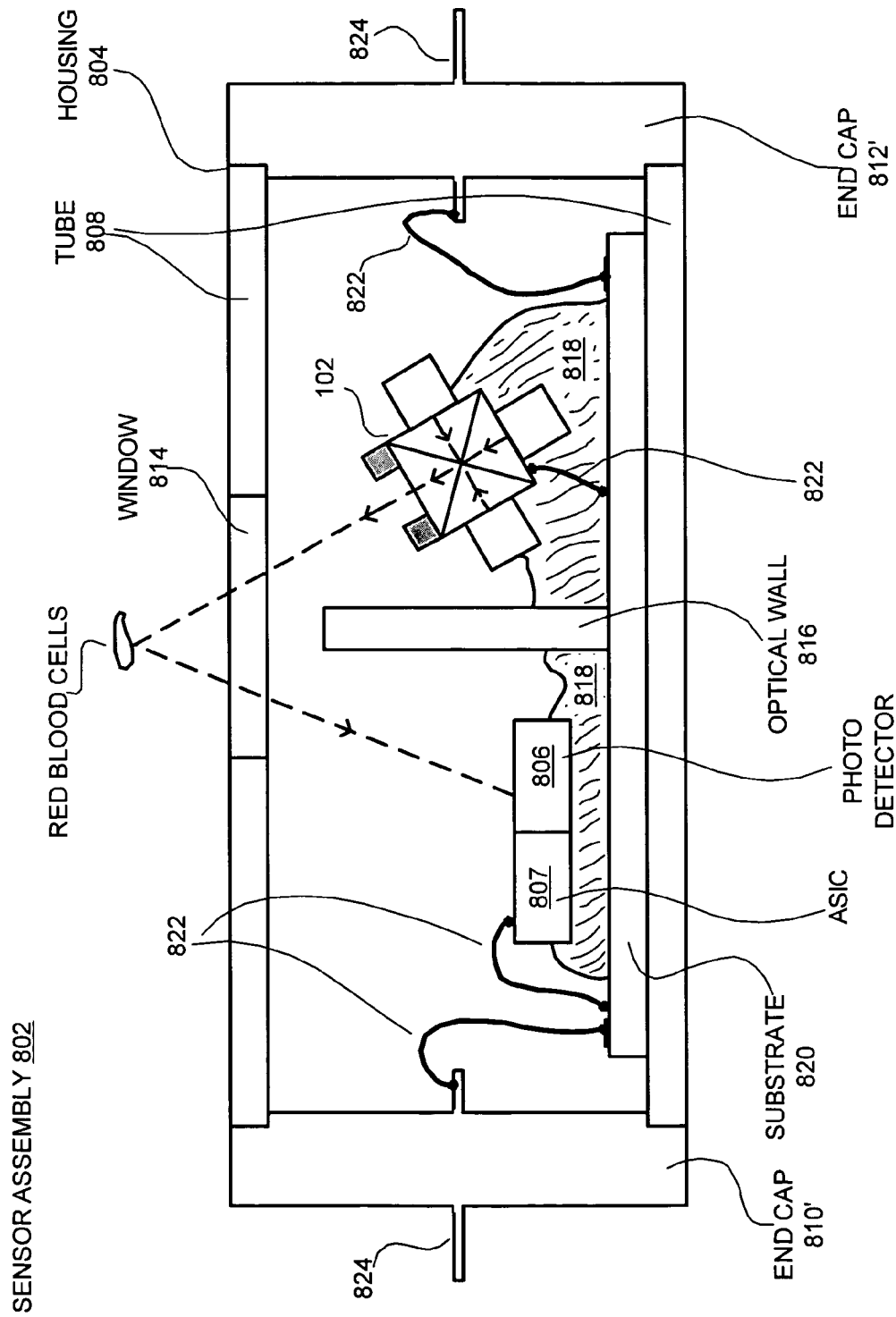
FIG. 8B illustrates an implantable oximetry sensor, according to another embodiment of the present invention.

In accordance with embodiments of the present invention, the beam combiner assemblies discussed above can be built into a sensor assembly 802, such as those shown in FIGS. 8A and 8B. The sensor 802, in turn, can be built into an implantable lead 902, such as that shown in FIG. 9.

Referring to FIG. 8A, in accordance with an embodiment of the present invention the sensor assembly 802 includes a sensor enclosure or housing 804 within which are one of the beam combiner structures discussed above, a photo detector 806 and an optional application specific integrated circuit (ASIC) 807. In FIG. 8A, the beam combiner 102 is shown. However, any of the other beam combiners 202, 302, 402, 502, 602 and 702 may alternatively be used. In accordance with an embodiment of the present invention, the housing 804 includes a tube 808 and a pair of end caps 810 and 812 that can be used to hermetically seal the components within the housing 802. The tube 808 can be made of an opaque material, such as metal (e.g., titanium or stainless steel) or ceramic, so long as it includes a window 814 that passes light of all the wavelengths of interest in the combined light beam (e.g., 130). In an alternative embodiment, the entire tube 808 can be made of a material that passes light of all the wavelengths of interest in the combined beam, and thus, in this embodiment the entire tube can be considered a window. The window 814 can for example be made of synthetic sapphire or some other appropriate material that passes light of all the wavelengths of interest. Alternatively, the entire tube 808 can be made from synthetic sapphire or some other appropriate material that passes light of all the wavelengths of interest. Exemplary synthetic sapphires are marketed by Imetra, Inc. (Elmsford, N.Y.) and Swiss Jewel (Philadelphia, Pa.).

The beam combiner structure (e.g., 102), the window 814 and the photo detector 806 should be positioned such that the combined light beam produced by the beam combiner exits the housing 804 through the window 814 and such that the light backscattered from blood (outside the window) will be scattered back toward the photo detector 806. The optional ASIC 807, which can include filters, analog-to-digital circuitry, multiplexing circuitry, and the like, controls the light sources and processes the photo detector signals produced by the photo detector 806 in any manner well known in the art. The ASIC 807 preferably provides digital signals indicative of the photo detector signals to an implantable device, such as an implantable monitor, pacemaker, or ICD. If the ASIC 807 or equivalent circuitry is not included within the sensor, analog signals can be delivered between the sensor 802 and the implantable device. However, it is preferred that digital signals are sent to and from the sensor 802 because digital signals are less susceptible to noise and other degradation.

An opaque optical wall 816 is positioned between the beam combiner structure 102 and the photo detector 806, so that light is not internally reflected from the beam combiner 102 to the photo detector 806. The beam combiner 102, optical wall 816, photo detector 806 and ASIC 807 can be attached to a substrate 820, e.g., by an epoxy 818. The substrate can be, e.g., a printed circuit board (PCB). Bond wires 822 can be used to attach the various components to the substrate 820, as well as to attach the substrate 820 to terminals 824 which extend through an insulated feedthrough 826 in the end cap 810. The housing 804, the feedthrough 826 and the endcaps 810 and 812 preferably provide hermeticity. In an alternative embodiment, shown in FIG. 8B, the endcaps 810' and 812' are made of a conductive material, and the tube 808 is made of a nonconductive material (so that the endcaps are electrically isolated from one another). In such an embodiment, there is no need for the feedthrough 826 shown in FIG. 8A because the terminals 824 can be connected directly to the conductive endcaps 810' and 812'. Nevertheless, a feedthrough may be used in the embodiment of FIG. 8B if desired.

Referring now to FIG. 9, in accordance with specific embodiments of the present invention, the sensor module 802 is built into an implantable lead 902. Accordingly, in this embodiment, the housing 804 of the sensor module 802 is sized to fit within the implantable lead 902. More specifically, the size of the beam combiner is preferably about 2 millimeters (mm) or less, and the size (shown as "d" in FIG. 10) of the sensor module 802 is about 4 mm or less, and preferably about 3 mm. The length of the sensor module 802, which extends axially in the lead 902 can be somewhat larger, because the length of the lead 902 is relatively large as compared to the diameter of the lead.

Further, the portion of the lead 902 that is adjacent to the window of the 814 of the sensor module, where light is to exit and enter, should allow the light to pass in and out of the sensor 802. Thus, the lead 902 may be transparent, or include its own window, opening, or the like. The lead 902 is shown as including tines 912 for attaching the lead in its desired position, but may include any other type of fixation means, or none at all. Additionally, the lead 902 may also include a lumen 916 for a stylet, which can be used for guiding the lead to its desired position. Also shown in FIG. 9 are wires 914 that provide power and possibly control signals to the sensor 802 from an implantable device, and provide pulse oximetry signals from the sensor 802 to the implantable device. As discussed below, preferably there are only two wires 914, but there may be more. If the sensor 802 of FIG. 8B is used, then one wire 914 is attached to the terminal 824 that extends from the endcap 810', while another wire 914 is attached to the terminal 824 that extends from the other endcap 812'.

The lead 902 can be, e.g., an implantable right atrial lead for implant in a patient's right atrial appendage, a right ventricular lead for transvenous insertion into the heart, a coronary sinus lead for placement in the coronary sinus region, or some other lead. The lead 902 can be implanted in or near a patient's heart, but this is not necessary. The exemplary lead 902 shown in FIG. 9 is a right ventricular lead that includes a ring electrode 908 and a tip electrode 910 that are connected to an implantable device by way of wires 904 and 906. Instead of being placed in a lead that includes cardiac electrodes, the sensor can be within a catheter intended for placement in a blood vessel or other blood confining space.

Referring now to FIG. 10, which is a rough cross-sectional view along the dashed line shown in FIG. 9, in accordance with an embodiment of the present invention the tube portion 808 of the sensor housing 804 is generally "D" shaped, so that it can be readily included with the implantable lead 902, while still allowing the lumen 916 (for a stylet) and wires 904 and 906 to fit within the same inner-space of the lead 902. Alternative shapes are also within the scope of the present invention. If the sensor 802 of FIG. 8B is used, then one of the wires 914 would also be seen in the cross-section of FIG. 10.

After the ASIC 807 controls the light sources the processes signals produced by the photo detector 806 in a manner well known in the art, it delivers signals indicative of the intensity of the detected light to an implantable device, an example of which is discussed below with reference to FIGS. 11A and 11B. The implantable device further processes the signal, e.g., for diagnostic and/or therapeutic use. Preferably, the ASIC 807 has all electronics to provide a two-wire 914 digital interface to the implantable device, as shown in FIG. 9. Further, one of the two sensor wires 914 may be combined with one of the pacing electrode wires 904 or 906 so that only three total wires are needed. Even further, a more complex 2-wire approach could use sub-pacing threshold signals between the implantable device and the sensor 802 using the same two wires 904 and 906 that connect to the pacing electrodes 908 and 910 resulting in a total of two wires in the lead 902 to the implantable device.

The lead 902 within which the sensor 802 is contained is attached to an implantable device. It is also possible that the sensor 802 is within a self contained hermetically sealed housing that communicates wirelessly with the implantable device. As mentioned above, the implantable device can be, e.g., a monitor, pacemaker, or ICD. For completeness, an exemplary implantable device 1110, that can be used to perform pacing, detect an arrhythmia, perform anti-arrhythmia therapy, detect specific cardiac events, etc., is described with reference to FIGS. 11A and 11B.

In accordance with embodiments of the present invention, the components are hermitically sealed within the sensor 802. Preferably the only elements running to and from the sensor 802 are wires 914 for providing power and possibly control signals to the sensor 802, and receiving pulse oximetry signals from the sensor 802.

In accordance with other embodiments of the present invention, the oximetry sensor module 802 is located within the housing of an implantable device that includes a window through which light can be transmitted and received. In still another embodiment, the oximetry sensor module 802 is in its own hermetically sealed housing that is attached directly to an implantable cardiac device. Additional details of how this can be accomplished are provided in commonly assigned U.S. patent application Ser. No. 10/913,942, entitled "Autonomous Sensor Modules for Patient Monitoring" (Turcott et al.), filed Aug. 5, 2004, which is incorporated herein by reference.

Exemplary Stimulation Device

Figure 11A:
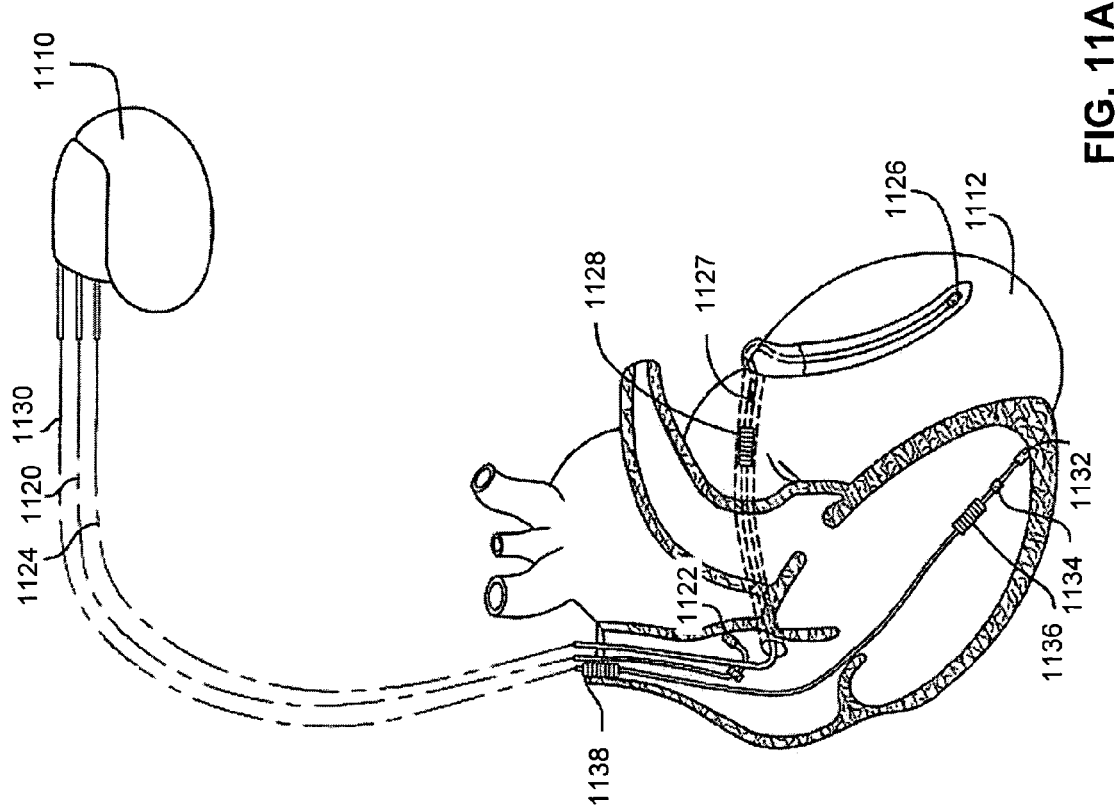
FIG. 11A illustrates an exemplary implantable stimulation device in electrical communication with a patient's heart by way of three leads, which are suitable for delivering multi-chamber stimulation and shock therapy.

Referring to FIG. 11A, the exemplary implantable stimulation device 1110 is shown as being in electrical communication with a patient's heart 1112 by way of three leads, 1120, 1124 and 1130, suitable for delivering multi-chamber stimulation and shock therapy. The sensor module 802 of the present invention can be placed within any of these leads, as was described above. Alternatively, a further dedicated lead or catheter can be provided for the purpose of containing the sensor 802 and placing the sensor 802 at a desired measurement site.

To sense atrial cardiac signals and to provide right atrial chamber stimulation therapy, the stimulation device 1110 is coupled to an implantable right atrial lead 1120 having at least an atrial tip electrode 1122, which typically is implanted in the patient's right atrial appendage.

To sense left atrial and ventricular cardiac signals and to provide left-chamber pacing therapy, the stimulation device 1110 is coupled to a "coronary sinus" lead 1124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The exemplary coronary sinus lead 1124 is designed to receive atrial and ventricular cardiac signals and to deliver left ventricular pacing therapy using at least a left ventricular tip electrode 1126, left atrial pacing therapy using at least a left atrial ring electrode 1127, and shocking therapy using at least a left atrial coil electrode 1128.

The stimulation device 1110 is also shown in electrical communication with the patient's heart 1112 by way of an implantable right ventricular lead 1130 having, in this embodiment, a right ventricular tip electrode 1132, a right ventricular ring electrode 1134, a right ventricular (RV) coil electrode 1136, and an SVC coil electrode 1138. Typically, the right ventricular lead 1130 is transvenously inserted into the heart 1112 so as to place the right ventricular tip electrode 1132 in the right ventricular apex so that the RV coil electrode 1136 will be positioned in the right ventricle and the SVC coil electrode 1138 will be positioned in the superior vena cava. Accordingly, the right ventricular lead 1130 is capable of receiving cardiac signals and delivering stimulation in the form of pacing and shock therapy to the right ventricle.

Figure 11B:
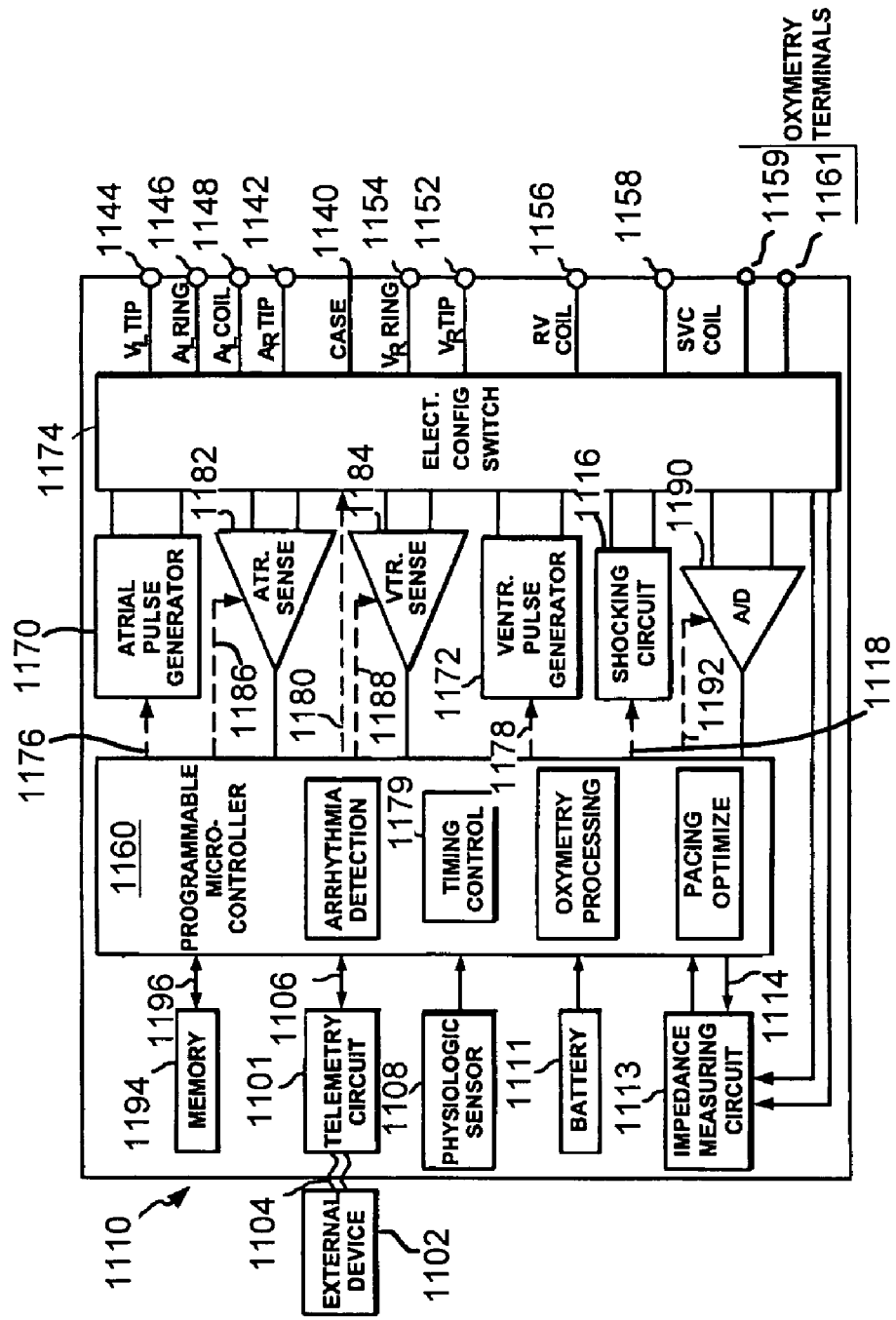
FIG. 11B is a simplified block diagram of the multi-chamber implantable stimulation device of FIG. 11A.

As illustrated in FIG. 11B, a simplified block diagram is shown of the multi-chamber implantable stimulation device 1110, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 1140 for the stimulation device 1110, shown schematically in FIG. 11B, is often referred to as the "can", "case" or "case electrode" and may be programmably selected to act as the return electrode for all "unipolar" modes. The housing 1140 may further be used as a return electrode alone or in combination with one or more of the coil electrodes, 1128, 1136 and 1138, for shocking purposes. The housing 1140 further includes a connector (not shown) having a plurality of terminals, 1142, 1144, 1146, 1148, 1152, 1154, 1156, and 1158 (shown schematically and, for convenience, the names of the electrodes to which they are connected are shown next to the terminals).

As such, to achieve right atrial sensing and pacing, the connector includes at least a right atrial tip terminal (AR TIP) 1142 adapted for connection to the atrial tip electrode 1122.

To achieve left chamber sensing, pacing and shocking, the connector includes at least a left ventricular tip terminal (VL TIP) 1144, a left atrial ring terminal (AL RING) 1146, and a left atrial shocking terminal (AL COIL) 1148, which are adapted for connection to the left ventricular tip electrode 1126, the left atrial ring electrode 1127, and the left atrial coil electrode 1128, respectively.

To support right chamber sensing, pacing and shocking, the connector further includes a right ventricular tip terminal (VR TIP) 1152, a right ventricular ring terminal (VR RING) 1154, a right ventricular shocking terminal (RV COIL) 1156, and an SVC shocking terminal (SVC COIL) 1158, which are adapted for connection to the right ventricular tip electrode 1132, right ventricular ring electrode 1134, the RV coil electrode 1136, and the SVC coil electrode 1138, respectively.

The connector is also shown as including terminals 1159 and 1161 (OXIMETRY TERMINALS), which are configured for connection to the wires 914 that are connected to the sensor module 802, to support the delivery of control signals to the sensor module 802, and to collect oximetry data from the sensor module 802.

At the core of the stimulation device 1110 is a programmable microcontroller 1160 which controls the various modes of stimulation therapy, including pacing optimization and anti-arrhythmia therapy. The microcontroller 1160 can also determine measures of blood oxygen saturation based on the signals it receives from an oximetry sensor of the present invention. Such measures of oxygen saturation can be used, e.g., for pacing optimization, disease monitoring, and the like. Additionally or alternatively, the measures of oxygen saturation can be stored in memory 1194 for later transmission to an external device 1102 using the telemetry circuit 1101.

If the oximetry sensor module 802 provides analog signals to the implantable device, then the terminals 1159 and 1161, through switch 1174, can provide such signals to an analog-to-digital (A/D) converter 1190 that converts the signals to a digital format understood by the microcontroller 1160. It is also possible that a dedicated ND converter be provided within the implantable device 1110 for the purpose of digitizing signals received from the oximetry sensor. If the oximetry sensor 802 provides digital signals to the implantable device 1110, then such signals may be provided directly to the microcontroller 1110, assuming it is the microcontroller 1160 that performs the processing that determines measures of blood oxygen saturation based on the signals. It is also possible that the implantable device 1110 include circuitry, external to the microcontroller 1160, which is dedicated to determining measures of blood oxygen saturation.

As is well known in the art, the microcontroller 1160 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 1160 includes the ability to analyze signals (data) as controlled by a program code stored in a designated block of memory. The details of the design of the microcontroller 1160 are not critical to the present invention. Rather, any suitable microcontroller 1160 can be used to carry out the functions described herein. The use of microprocessor-based control circuits for performing timing, control and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Thornander et al.)

and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 11B, an atrial pulse generator 1170 and a ventricular pulse generator 1172 generate pacing stimulation pulses for delivery by the right atrial lead 1120, the right ventricular lead 1130, and/or the coronary sinus lead 1124 via an electrode configuration switch 1174. It is understood that in order to provide stimulation therapy in each of the four chambers of the heart, the atrial and ventricular pulse generators, 1170 and 1172, may include dedicated, independent pulse generators, multiplexed pulse generators, or shared pulse generators. The pulse generators, 1170 and 1172, are controlled by the microcontroller 1160 via appropriate control signals, 1176 and 1178, respectively, to trigger or inhibit the stimulation pulses.

The microcontroller 1160 further includes timing control circuitry 1179 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 1174 includes a plurality of switches for connecting the desired electrodes to the appropriate I/O circuits, thereby providing complete electrode programmability. Accordingly, the switch 1174, in response to a control signal 1180 from the microcontroller 1160, determines the polarity of the stimulation pulses (e.g., unipolar, bipolar, combipolar, etc.) by selectively closing the appropriate combination of switches (not shown) as is known in the art. The switch 1174 can also be used to connect wires from an oximetry sensor 802 to appropriate I/O circuits.

Atrial sensing circuits 1182 and ventricular sensing circuits 1184 may also be selectively coupled to the right atrial lead 1120, coronary sinus lead 1124, and the right ventricular lead 1130, through the switch 1174 for detecting the presence of cardiac activity in each of the four chambers of the heart. Accordingly, the atrial (ATR. SENSE) and ventricular (VTR. SENSE) sensing circuits, 1182 and 1184, may include dedicated sense amplifiers, multiplexed amplifiers, or shared amplifiers. The switch 1174 determines the "sensing polarity" of the cardiac signal by selectively closing the appropriate switches, as is also known in the art. In this way, the clinician may program the sensing polarity independent of the stimulation polarity.

Each sensing circuit, 1182 and 1184, preferably employs one or more low power, precision amplifiers with programmable gain and/or automatic gain control, bandpass filtering, and a threshold detection circuit, as known in the art, to selectively sense the cardiac signal of interest. The automatic gain control enables the device 1110 to deal effectively with the difficult problem of sensing the low amplitude signal characteristics of atrial or ventricular signals.

The outputs of the atrial and ventricular sensing circuits, 1182 and 1184, are connected to the microcontroller 1160 which, in turn, are able to trigger or inhibit the atrial and ventricular pulse generators, 1170 and 1172, respectively, in a demand fashion in response to the absence or presence of cardiac activity, in the appropriate chambers of the heart. The sensing circuits, 1182 and 1184, in turn, receive control signals over signal lines, 1186 and 1188, from the microcontroller 1160 for purposes of measuring cardiac performance at appropriate times, and for controlling the gain, threshold, polarization charge removal circuitry (not shown), and timing of any blocking circuitry (not shown) coupled to the inputs of the sensing circuits, 1182 and 1186.

For arrhythmia detection, the device 1110 utilizes the atrial and ventricular sensing circuits, 1182 and 1184, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 1160 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 1190. The data acquisition system 1190 is configured to acquire intracardiac electrogram signals, convert the raw analog data into a digital signal, and store the digital signals for later processing and/or telemetric transmission to an external device 1102. The data acquisition system 1190 is coupled to the right atrial lead 1120, the coronary sinus lead 1124, and the right ventricular lead 1130 through the switch 1174 to sample cardiac signals across any pair of desired electrodes.

Advantageously, the data acquisition system 1190 can be coupled to the microcontroller 1160, or other detection circuitry, for detecting an evoked response from the heart 1112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 1160 detects a depolarization signal during a window following a stimulation pulse, the presence of which indicates that capture has occurred. The microcontroller 1160 enables capture detection by triggering the ventricular pulse generator 1172 to generate a stimulation pulse, starting a capture detection window using the timing control circuitry 1179 within the microcontroller 1160, and enabling the data acquisition system 1190 via control signal 1192 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Kleks et. al.), which patents are hereby incorporated herein by reference. The type of capture detection system used is not critical to the present invention.

The microcontroller 1160 is further coupled to a memory 1194 by a suitable data/address bus 1196, wherein the programmable operating parameters used by the microcontroller 1160 are stored and modified, as required, in order to customize the operation of the stimulation device 1110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 1112 within each respective tier of therapy.

Data acquired by the data acquisition system 1190 (and optionally stored) can be used for subsequent analysis to guide the programming of the device and/or to monitor oxygen saturation, appropriately adjust pacing interval parameters, select optimum pacing intervals, and/or select appropriate anti-arrhythmia therapy.

Advantageously, the operating parameters of the implantable device 1110 may be non-invasively programmed into the memory 1194 through a telemetry circuit 1101 in telemetric communication with the external device 1102, such as a programmer, transtelephonic transceiver, or a diagnostic system analyzer. The telemetry circuit 1101 is activated by the microcontroller by a control signal 1106. The telemetry circuit 1101 advantageously allows intracardiac electrograms, oxygen saturation information and status information relating to the operation of the device 1110 (as contained in the microcontroller 1160 or memory 1194) to be sent to an external device 1102 through an established communication link 1104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (note: this relates to transfer of EGM data) (McClure et al.), which patents are hereby incorporated herein by reference.

The stimulation device 1110 can further include one or more physiologic sensors 1108, which can be located within the stimulation device housing 1140 as shown, or can be located external to the housing.

The stimulation device 1110 additionally includes a battery 1111 which provides operating power to all of the circuits shown in FIG. 11B. For the stimulation device 1110, which employs shocking therapy, the battery 1111 must be capable of operating at low current drains for long periods of time, and then be capable of providing high-current pulses (for capacitor charging) when the patient requires a shock pulse. The battery 1111 should also have a predictable discharge characteristic so that elective replacement time can be detected. Accordingly, the device 1110 preferably employs lithium/silver vanadium oxide batteries, but is not limited thereto.

The stimulation device 1110 can further include a magnet detection circuitry (not shown), coupled to the microcontroller 1160. It is the purpose of the magnet detection circuitry to detect when a magnet is placed over the stimulation device 1110, which magnet may be used by a clinician to perform various test functions of the stimulation device 1110 and/or to signal the microcontroller 1160 that the external programmer 1102 is in place to receive or transmit data to the microcontroller 1160 through the telemetry circuits 1101.

As further shown in FIG. 11B, the device 1110 is shown as having an impedance measuring circuit 1113 which is enabled by the microcontroller 1160 via a control signal 1114. The known uses for an impedance measuring circuit 1113 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 1113 is advantageously coupled to the switch 1174 so that any desired electrode may be used. In addition, to facilitate the measurement of peripheral tissue edema, extra electrodes can be added to the device housing, thereby limiting the test electric field to the peripheral tissue.

In the case where the stimulation device 1110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 1160 further controls a shocking circuit 1116 by way of a control signal 1118. The shocking circuit 1116 generates shocking pulses of low (up to 0.5 Joules), moderate (0.5-10 Joules), or high energy (11 to 40 Joules), as controlled by the microcontroller 1160. Such shocking pulses are applied to the patient's heart 1112 through at least two shocking electrodes, and as shown in this embodiment, selected from the left atrial coil electrode 1128, the RV coil electrode 1136, and/or the SVC coil electrode 1138. As noted above, the housing 1140 may act as an active electrode in combination with the RV electrode 1136, or as part of a split electrical vector using the SVC coil electrode 1138 or the left atrial coil electrode 1128 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of ventricular fibrillation. Accordingly, the microcontroller 1160 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An implantable multi-wavelength oximetry sensor, comprising:
   an implantable sensor housing defining a window through which light can pass;
   a first light source, within said sensor housing, to transmit light having a first wavelength;
   a second light source, within said sensor housing, to transmit light having a second wavelength; and
   a plurality of prisms within said sensor housing, each prism including a plurality of surfaces;
   a dichroic surface formed on a first surface of one of said prisms;
   wherein said dichroic surface reflects light of the first wavelength and passes light of the second wavelength;
   wherein said first light source is mounted to a second surface of a first one of said prisms directly, or with a first lens therebetween such that said first light source is mounted to one side of said first lens and another side of said first lens is mounted to the second surface of said first one of said prisms;

wherein said second light source is mounted to a second surface of a second one of said prisms directly, or with a second lens therebetween such that said second light source is mounted to one side of said second lens and another side of said second lens is mounted to the second surface of said second one of said prisms; and wherein said dichroic surface is angled relative to said first light source and said second light source such that light of the first wavelength transmitted by said first light source is reflected to travel in generally a same direction as light of the second wavelength transmitted by said second light source that passes through said dichroic surface; and wherein said surface on which said dichroic surface is formed is different than both said surface to which said first light source is mounted and said surface to which said second light source is mounted.

2. The sensor of claim 1, wherein said plurality of prisms are bonded together to form a three dimensional structure having inner surfaces where a pair of said prisms meet, and wherein said dichroic surface is formed on one of said inner surfaces.

3. The sensor of claim 2, wherein said three dimensional structure also has outer surfaces, and wherein said first and second light sources are mounted to two of said outer surfaces of said three dimensional structure.

4. The sensor of claim 2, wherein said plurality of prisms are bonded together by an optical cement or another clear epoxy.

5. The sensor of claim 3, wherein said three-dimensional structure, formed by said plurality of prisms bonded together, is cubical, rectangular or trapezoidal.

6. The sensor of claim 3, wherein light of the first wavelength that is reflected by said dichroic surface, and light of the second wavelength that passes through said dichroic surface, exit said three dimensional structure through one of said outer surfaces, which said one of said outer surfaces is concave to increase an exit angle.

7. The sensor of claim 1, wherein said window is positioned relative to said dichroic surface such that light of the first wavelength that is reflected by said dichroic surface, and light of the second wavelength that passes through said dichroic surface, exit said housing through said window.

8. The sensor of claim 7, further comprising:
a light detector, within said sensor housing, to detect light of the first wavelength and light of the second wavelength scattered by blood back into said housing through said window.

9. The sensor of claim 1, wherein said implantable sensor housing is sized to fit within an implantable catheter or cardiac lead.

10. The sensor of claim 9, wherein said housing includes:
a tube within which said first and second light sources and said prisms are located; and
a first end cap to enclose a first end of said tube; and
a second end cap to enclose a second end of said tube.

11. The sensor of claim 1, further comprising:
a third light source, within said sensor housing, to transmit light having a third wavelength; and
a second dichroic surface, formed on one of said prisms within said sensor housing, that reflects light having the third wavelength, passes light of the first wavelength, and passes light of the second wavelength;

wherein said second dichroic surface is angled relative to said first, second and third light sources and said first dichroic surface such that light of the third wavelength transmitted by said third light source is reflected to travel in generally a same direction as light of the first wavelength reflected by said first dichroic surface and light of the second wavelength that passes through said first dichroic surface and said second dichroic surface.

12. An implantable multi-wavelength oximetry sensor, comprising:
an implantable sensor housing including a window through which light can pass;
a first light source, within said sensor housing, to transmit light having a first wavelength;
a second light source, within said sensor housing, to transmit light having a second wavelength;
a plurality of prisms within said sensor housing;
a first dichroic surface, formed on a surface of a first one of said prisms within said sensor housing, that reflects light of the first wavelength and passes light of the second wavelength;
a second dichroic surface, formed on a surface of a second one of said prisms within said sensor housing, that reflects light of the second wavelength and passes light of the first wavelength;
wherein said plurality of prisms are bonded together to form a three dimensional structure having inner surfaces where pairs of said prisms meet;
wherein said first dichroic surface is formed on one of said inner surfaces and said second dichroic surface is formed on another one of said inner surfaces;
wherein said three dimensional structure also has outer surfaces;
wherein said first light source is mounted to a said outer surface directly, or with a first lens therebetween; and
wherein said second light source is mounted to another said outer surface directly, or with a second lens therebetween; and
wherein said first and second dichroic surfaces are angled relative to said first and second light sources such that light of the first wavelength transmitted by said first light source is reflected by said first dichroic surface to travel in generally a same direction as light of the second wavelength transmitted by said second light source that is reflected by said second dichroic surface.

13. The sensor of claim 12, wherein said three-dimensional structure is cubical, rectangular or trapezoidal.

14. The sensor of claim 12, wherein light of the first wavelength that is reflected by said first dichroic surface, and light of the second wavelength that is reflected by said second dichroic surface, exit said three dimensional structure through one of said outer surfaces, which said one of said outer surfaces is concave to increase an exit angle.

15. The sensor of claim 12, wherein said window is positioned relative to said first and second dichroic surfaces such that light of the first wavelength that is reflected by said first dichroic surface, and light of the second wavelength that is reflected by said second dichroic surface, exit said housing through said window.

16. The sensor of claim 15, further comprising:
a light detector, within said sensor housing, to detect light of the first wavelength and light of the second wavelength scattered by blood back into said housing through said window.

17. The sensor of claim 12, further comprising:
a third light source, within said sensor housing, to transmit light having a third wavelength; and wherein said first and second dichroic surfaces pass light of the third wavelength; and wherein light of the third wavelength transmitted by said third light source, which passes through said first and second dichroic surfaces, travels is generally a same direction as light of the first wavelength reflected by said first dichroic surface and light of the second wavelength reflected by said second dichroic surface.

18. An implantable apparatus, comprising:

an elongated flexible body configured to be implanted in a blood vessel or a chamber of a heart;

an implantable sensor within said elongated flexible body, said implantable sensor including a sensor housing and a window through which light can enter and exit said sensor housing;

a plurality of prisms, within said sensor housing, said prisms bonded together to form a three dimensional structure;

a plurality of light sources mounted to said three dimensional structure, within said sensor housing, each of which transmits light of a different wavelength; and one or more inner surfaces of said three dimensional structure, within said sensor housing, configured to combine the light from said plurality of light sources into a beam of light for transmission through said window of said sensor housing.

19. The apparatus of claim 18, wherein said elongated flexible body includes a portion through which light can exit and enter said flexible body.

20. The apparatus of claim 18, wherein said one or more inner surfaces comprise one or more dichroic surfaces.

21. The apparatus of claim 20, wherein each said dichroic surface is formed on a said prism.

22. The apparatus of claim 18, wherein at least one of said one or more surfaces relies on critical angle reflection to reflect light from one of said plurality of light sources.

23. The apparatus of claim 18, further comprising:

a light detector, within said sensor housing, to detect light scattered by blood back into said housing through said window of said sensor housing.

24. The sensor of claim 18, wherein said plurality of prisms are bonded together by an optical cement or another clear epoxy.

25. The apparatus of claim 18, wherein one or more of said plurality of light sources are mounted directly to said three dimensional structure.

26. The apparatus of claim 18, wherein one or more of said plurality of light sources are mounted to said three dimensional structure with a lens therebetween.

27. The apparatus of claim 18, wherein said three-dimensional structure, formed by said plurality of prisms bonded together, is cubical, rectangular or trapezoidal.

* * * * *

UNITED STATES PATENT AND TRADEMARK OFFICE
CERTIFICATE OF CORRECTION

| | | |
|---|---|---|
| PATENT NO. | : 7,660,616 B1 | Page 1 of 1 |
| APPLICATION NO. | : 11/231555 | |
| DATED | : February 9, 2010 | |
| INVENTOR(S) | : John W. Poore | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Signed and Sealed this

Thirtieth Day of November, 2010

David J. Kappos
*Director of the United States Patent and Trademark Office*